United States Patent
Kliewer et al.

(12)

(10) Patent No.: US 6,572,606 B2
(45) Date of Patent: Jun. 3, 2003

(54) LASER FLUENCE COMPENSATION OF A CURVED SURFACE

(75) Inventors: Michael L. Kliewer, Ocoee, FL (US); Michael J. Smith, Orlando, FL (US)

(73) Assignee: LaserSight Technologies, Inc., Winter Park, FL (US)

( * ) Notice: Subject to any disclaimer, the term of this patent is extended or adjusted under 35 U.S.C. 154(b) by 196 days.

(21) Appl. No.: 09/757,794

(22) Filed: Jan. 11, 2001

(65) Prior Publication Data

US 2001/0031960 A1 Oct. 18, 2001

Related U.S. Application Data

(60) Provisional application No. 60/175,634, filed on Jan. 12, 2000, and provisional application No. 60/196,290, filed on Apr. 12, 2000.

(51) Int. Cl.[7] ............................................. A61F 9/007
(52) U.S. Cl. ................................ 606/5; 606/10; 606/13
(58) Field of Search ............................ 606/3, 5, 10–14

(56) References Cited

U.S. PATENT DOCUMENTS

| | | | |
|---|---|---|---|
| 4,911,711 A | * | 3/1990 | Telfair .............................. 606/5 |
| 5,219,344 A | * | 6/1993 | Yoder, Jr. ......................... 606/5 |
| 6,090,100 A | * | 7/2000 | Hohla ............................. 606/5 |

* cited by examiner

Primary Examiner—David M. Shay
(74) Attorney, Agent, or Firm—William H. Bollman

(57) ABSTRACT

A laser system and techniques which compensate for laser fluence drop off or losses of irradiation as an ablating laser beam is traversed on a curved surface (e.g., on corneal tissue). The disclosed ablating laser system and techniques compensate for fluence differentials from pulse-to-pulse by adjusting an appropriate parameter of a laser beam. In the preferred embodiment, the number of pulses imparted in the periphery, the size or shape of the ablating laser beam is adjusted with, e.g., a variable aperture placed in the beam delivery path, by changing a magnification of relay optics in the beam delivery path, or by increasing a number of ablation spots in peripheral portions of an ablation zone as compared with the number of ablation spots in a central portion of the ablation zone. The fluence is compensated for using empirically measured or theoretical fluence correction factors given the angle of the laser beam, size and shape of the ablation spot, etc. In addition to magnification adjustment, the present invention also employs the technique of changing the size of the aperture that is imaged o the eye to provide uniform energy density (i.e., fluence) throughout the entire area of the irradiation site. These techniques are used independently or in conjunction to reshape the curvature of the eye to correct myopia, hyperopia, astigmatism or combinations thereof.

12 Claims, 5 Drawing Sheets

LASER FLUENCE COMPENSATION OF A CURVED SURFACE

The present application claims priority from U.S. Provisional Application No. 60/175,634, filed Jan. 12, 2000, entitled "Laser Fluence Compensation" to Michael L. Kliewer; and from U.S. Provisional Application No. 60/196,290, filed Apr. 12, 2000, entitled "Laser Fluence Compensation of a Curved Surface" to Michael L. Kliewer, the entirety of both of which are expressly incorporated herein by reference.

BACKGROUND OF THE INVENTION

1. Field of the Invention

The present invention relates to a laser surgery system. More particularly, it relates to a non-contact laser ablation method and apparatus providing laser fluence compensation of a curved surface, especially a corneal surface.

2. Background

The cornea and lens of an eye act in unison on light entering the eye to focus the incoming light onto the retina. When the refractive power of the cornea and lens are optimized for the length of the eye, a sharp image is focused on the retina. Myopia (nearsightedness) is the result of blurred images caused when the focal point of the image is located before the retina. Hyperopia (farsightedness) is the result of blurred images caused when the focal point of the image is behind the retina. Astigmatism is a unique refractive error that causes reduced visual acuity and produces symptoms such as glare, monocular diplopia, asthenopia and distortion and occurs when the focus from tangential light rays are at a different point than the focus of the sagital light rays.

Vision acuities result from refractive errors from the corneal of the eye and the lens within the globe of the eye. For example, nearsightedness, or myopia is a result of the shape of the corneal membrane being too steep.

One popular technique for correcting vision acuities is reshaping the cornea of the eye. The cornea is chosen for modification before other components of the eye because it is the strongest refracting component of the eye and is accessible without interoccular surgery. As an example, the cornea of a patient with hyperopia, or farsightedness is relatively flat resulting in a large spherical radius of the cornea. A flat cornea creates an optical system that does not correctly focus the viewed image onto the retina of the eye but in fact the focal point is beyond the surface of the retina. Hyperopia can be corrected by reshaping the eye to decrease the spherical radius of the cornea. In the case of correcting hyperopia, corneal tissue is typically not removed at the center of the cornea but is removed deeply at the periphery of the cornea.

As another example, to correct myopic effects of an eye, procedures are performed which effectively increase the radius of the cornea. In this case, the corneal surface is removed deeply at its center and slightly at its periphery.

In another example, such as the case of the correction of astigmatism (e.g., myopic astigmatism), the surface of the cornea is removed deeply at its center but only along a certain axis and slightly at its periphery. The resulting shape of the cornea is that of a cylindrical convex lens.

Changing ablation patterns on the cornea performs the various vision corrections. Use of an ablating laser beam for removing the surface of the cornea to correct ametropia of any sort requires precise administration of the laser beam.

Optical systems are commonly used to control or condition an ablating laser beam exiting from a laser source prior to impingement onto a corneal surface.

A common ablation laser system scans and pulsates an ablating laser beam across a corneal surface. Typically, the laser source is fixed in location with respect to the patient's eye, as is the patient. To remove corneal tissue throughout a given ablation pattern, the ablating laser beam is typically directed across the corneal surface with the use of scanning mirrors.

However, as is appreciated by the present invention, ablation of a curved surface introduces several dynamics that are typically unaccounted for in conventional laser ablation systems.

For instance, as shown in FIG. 4A, when the ablating laser beam is ablating a spot on the cornea directly below, a 'direct' hit on the cornea causes a maximum amount of energy absorption and transfer between the laser beam and the corneal tissue being treated. This is because a normal or perpendicular angle $\theta$ is formed between the laser beam and the surgical plane. However, as the angle of the laser beam with respect to the surgical plane changes from 90° as shown in FIG. 4B, less energy from the laser beam transfers to the corneal tissue, resulting in changing depths of ablation across the ablated curved surface.

Generally speaking, the eye is a spherical surface as depicted in FIGS. 4A and 4B, and the angle of incidence of the scanning laser beam on the eye varies as the with respect to distance from the apex of the eye. FIGS. 4A and 4B illustrate that the farther the apex of the laser beam is from the center of the targeted curved surface 10, the greater the angle of incidence $2\theta'$ of the laser beam due to the curved surface 10. This is especially true for small beam, scanning laser ablation systems, although it is also true for broad beam systems. The broad beam systems must compensate for the loss of power transferred to the cornea at the periphery.

FIG. 4B is illustrative of the reflection of additional laser energy off the curved irradiation site due to the enlarged spot size being projected onto the cornea.

As appreciated by the present inventor, as an ablating laser beam spot traverses a corneal surface, it tends to become elliptical on the curved surface, and assumes a larger area. Fluence is defined as energy over area, or energy density. Thus, as the laser beam angles steeper and steeper (i.e., further from a normal to the surgical plane) at the edges of a larger and larger ablation pattern, the fluence decreases. This is appreciated to result in ablation depths toward the edges of the ablation pattern which are less than the expected depth, and less than the ablation depth at a central portion of the ablation pattern at a point directly below a normal angled laser beam.

The increased depth per pulse in the central portion of the ablation pattern as opposed to the peripheral portions of the ablation pattern often cause the resulting shape to be non spherical and will change the prolate nature of the cornea. The non-uniform removal of tissue (e.g., corneal tissue) can produce an irregular corneal outer surface and may even prevent proper healing.

There is a need for an ablation apparatus and method, which provides greater control and uniformity of the depth of ablation across an ablation pattern on a curved surface such as a corneal surface.

SUMMARY OF THE INVENTION

In accordance with the principles of the present invention, an ablation laser system having variable fluence comprises a laser source, and relay optics for delivering a laser beam from the laser source to a target surface. The number of pulses is increased in the periphery to compensate for the reduced ablation due to reduced fluence in this region.

In accordance with another aspect of the present invention, an ablation laser system having variable fluence comprises a laser source, and relay optics for delivering a laser beam from the laser source to a target surface. An ablation spot fluence adjuster adjusts a fluence of an ablation pulse on the target surface.

In accordance with another aspect of the present invention, a system for imparting ablating laser radiation onto a target curved surface comprises a laser source having an output laser beam, and a variable aperture device. A controller is operatively connected to the aperture to adjust the diameter of the laser beam. Relay optics produce an image of the laser beam, and turning optics scan the image of the laser beam across the target surface.

A method for providing laser radiation on a curved surface having a desired fluence throughout in accordance with yet another aspect of the present invention comprises providing an ablating laser beam. A cross-sectional shape of the ablating laser beam is set to a first size, with respect to a particular ablation spot of a particular ablation pattern on a particular layer of tissue to provide a given fluence level for that particular ablation spot. The ablating laser beam is scanned to another ablation spot of the particular ablation pattern on the particular layer of tissue, and the cross-sectional shape of the ablating laser beam is re-adjusted to a second size different from the first size, with respect to another ablation spot, to maintain the given fluence level for the ablation spot.

BRIEF DESCRIPTION OF THE DRAWINGS

Features and advantages of the present invention will become apparent to those skilled in the art from the following description with reference to the drawings, in which.

DETAILED DESCRIPTION OF ILLUSTRATIVE EMBODIMENTS

The present invention recognizes the fluence differential of an ablating laser spot across a curved surface, and provides apparatus and methods to compensate for the decrease in fluence on the periphery of a curved ablated tissue surface, e.g., a cornea.

In accordance with the principles of the present invention, the fluence administered to an ablated surface is controlled and/or varied in relation to an angle between the impinging laser beam and the angle of the target surface at the relevant ablation spot.

In one embodiment, the size of the ablation spot image projected onto a surgical plane is controlled to maintain a particular fluence as the ablation spot scans across a target surface. The size of the ablation spot image may be varied, e.g., by adjusting relay optics that image the aperture on the eye (i.e., by changing the magnification power of the optics), or by simply changing the size of an aperture in the laser beam delivery path.

In any event, in accordance with the principles of the present invention, the fluence of the ablating laser beam on the eye is increased or decreased depending upon the angle of the laser beam and on the angle of the surface being treated at the point of the ablation spot being contemplated. Given those angles, the actual size of the spot, and thus the actual fluence at a particular ablation point can be more accurately determined, and adjusted to meet a predetermined fluence profile. As a result, the fluence of ablation spots (particularly toward the periphery of an ablation pattern) are actively controlled to be consistent with expected results (e.g., to maintain a consistent fluence for all ablation spots across an ablation pattern, resulting in consistency, uniformity, and predictability throughout any given ablation pattern.

The compensation can also be calculated beforehand in a planning exercise. The new ablation pattern with compensation can then be imparted onto the cornea.

There are four exemplary approaches employed by the present invention to achieve the desired pulse-by-pulse fluence control. In a first approach, the fluence of the beam image may be adjusted by adjusting the power of the laser beam. In a second approach, the size of the beam image impinged on the cornea may be adjusted to adjust the fluence. In a third approach, both laser power and beam size may be adjusted to achieve an appropriate beam image necessary for affecting the desired refractive correction. In the fourth method, the number of pulses incident upon the cornea are increased at the periphery in order to compensate for the decrease in fluence and ultimately the decrease in ablation depth.

Figure 1:
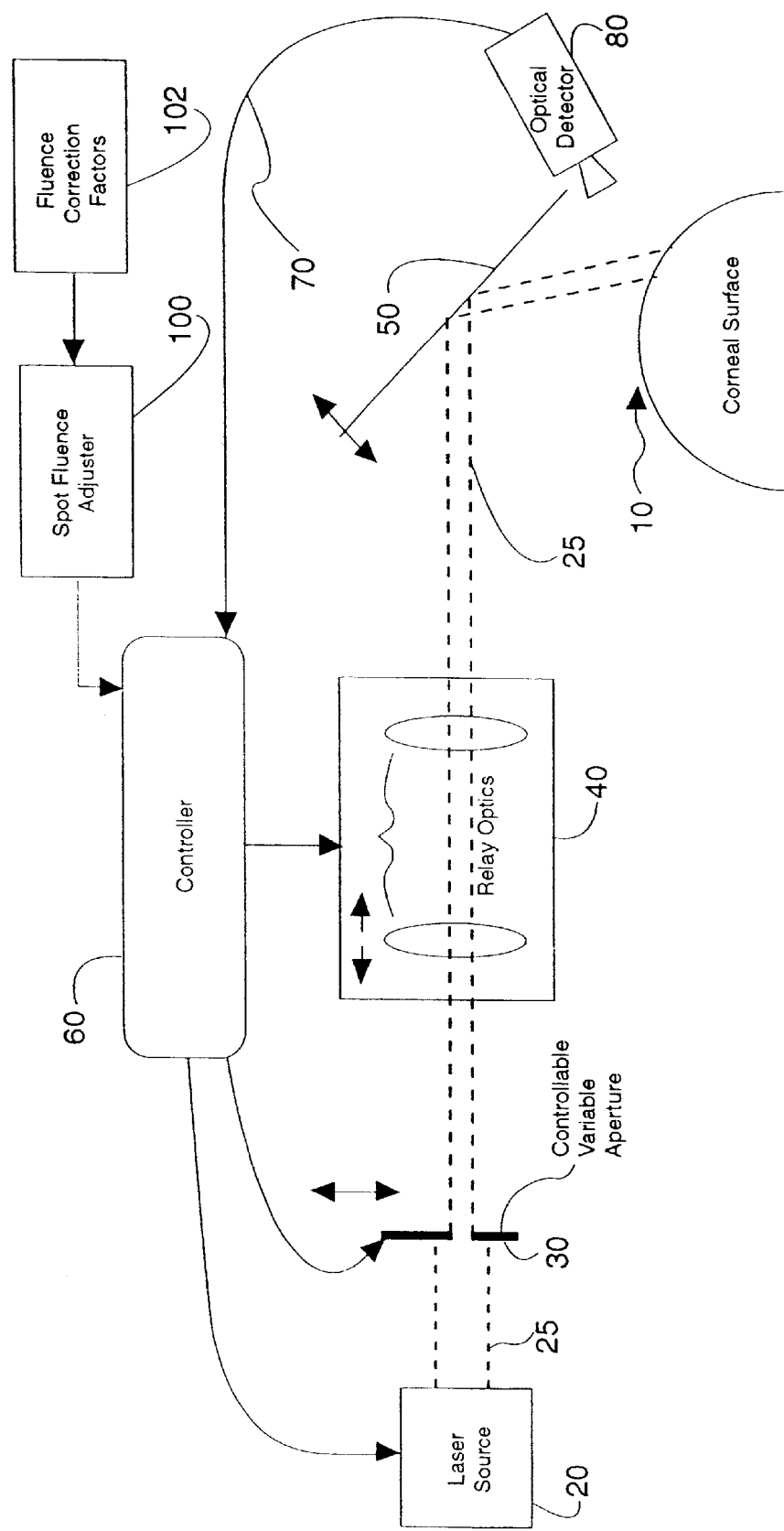
FIG. 1 illustrates a laser surgical system including an ablation spot fluence adjuster and fluence correction factors, in accordance with the principles of the present invention.

FIG. 1 illustrates a laser surgical system including an ablation spot fluence adjuster and fluence correction factors, in accordance with the principles of the present invention.

FIG. 1 depicts a block diagram of the ophthalmic laser system of a preferred embodiment. The laser source 20 is a basic laser, e.g., a basic, fundamentally ultraviolet laser such as an excimer laser. The laser source 20 produces a laser beam 25 which travels through an aperture 30 to relay optics 40 to produce an image of the beam 25'. A laser beam image 25' is coupled to a corneal surface 10 by the turning (scanning) optics 50. The turning optics are reflective or semi reflective optical elements which change the axis of the laser beam image 25' in two dimensions from that of the source to the axis of the corneal surface. The turning optics are reflective optics which may include mirrors, transmission optics with a highly reflective coating, or reflective coatings on reflective optics. Suitable scanners include galvanometers, mirror arrays, octagonal mirrors, etc.

A suitable controller 60 (e.g., a microprocessor, a microcontroller, or a digital signal processor (DSP)) controls the relay optics 40 and the aperture 30 with information provided by an optical detector 80. Data provided by an initial step of topography or wavefront may be used to provide the actual curvature and form the basis of a corrective procedure to be performed by the ophthalmic laser system. Of course, the invention also relates to non-custom ablation systems and techniques relying on more conventional refractive measurements of a patient's cornea, and presuming a given shape of the cornea.

The relay optics 40 are adjusted by control of the controller 60. The variable size aperture 30 may be adjusted to provide the appropriate beam size and energy densities to cause a desired actual fluence on the corneal membrane.

From a system standpoint, the invention can include a laser beam generating device or source 20 for producing a beam of radiation along a path, an aperture 30 for adjusting beam size (and thus fluence), and a beam imaging means comprising a relay lens system 40 for imaging a desired image of the laser beam onto the eye 10, and a spot fluence adjuster with appropriate fluence correction factors relating to specific angles of the laser beam and/or target surface.

The target surface may be any tissue surface having a curved surface, e.g., skin, cornea, etc. However, the preferred embodiment of the present invention relates to the reshaping of the cornea of an eye.

As above, in a first method of the present invention, the fluence may be adjusted by adjusting the relay optics 40 for a greater or lesser energy density. The relay optics 40 control the size of the laser beam. Since an image of the laser beam has been created by the relay optics 40, the fluence levels can be controlled and made constant throughout the image of the beam. When the laser beam is condensed, the energy deposited on the surface 10 increases. Alternatively, when the laser beam is expanded, the energy deposited on the surface decreases.

In a second technique, the energy density imparted on the corneal surface 10 is adjusted by fixing the size of the image of the laser beam accordingly. The size of the image of the laser beam is adjusted by adjusting the opening of the aperture 30 as indicated by the arrows in FIG. 3. By adjusting the size of the laser beam image as a function of the angle of incidence, a static energy density with the required beam profile can be achieved. The size of the image of the beam may be made larger or smaller by adjusting the aperture 30. This adjustment of the aperture may be carried out manually or by the microprocessor.

Figure 2:
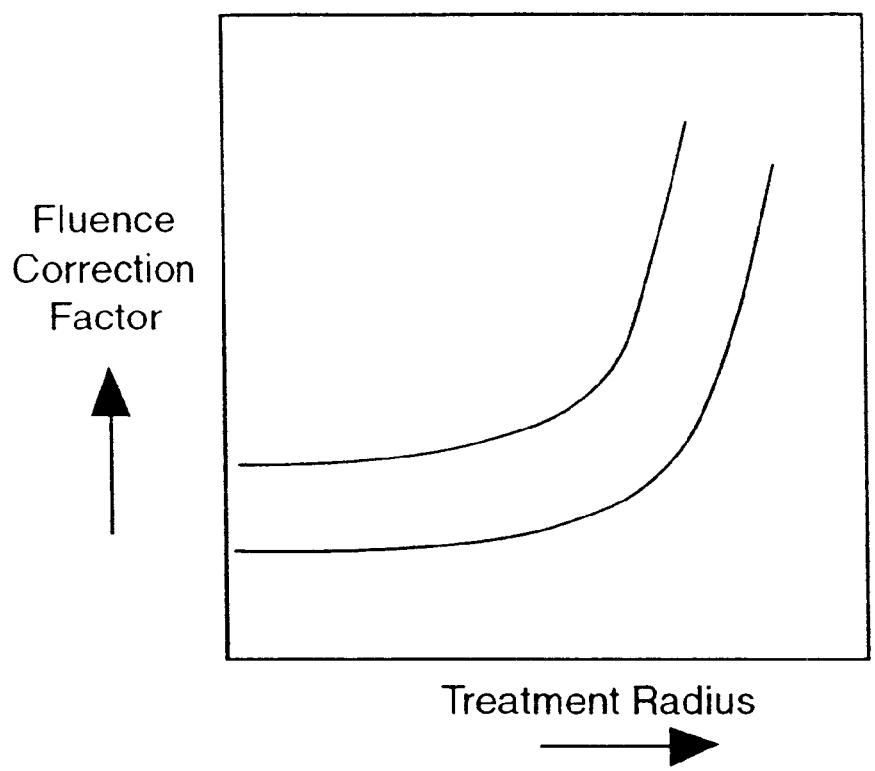
FIG. 2 is a graph representing exemplary correction factors used by a spot fluence adjuster for index and fluence as the angle versus treatment radius changes, in accordance with the principles of the present invention.

FIG. 2 is a graph representing exemplary correction factors used by a spot fluence adjuster for index and fluence as the angle versus treatment radius changes, in accordance with the principles of the present invention.

In particular, as shown in FIG. 2, the periphery portion of the ablation pattern is represented by an increasing treatment radius. As can be seen in FIG. 2, the fluence is increased as the treatment radius increases (i.e., as the angle of the laser beam off-normal increases, and/or as the tangent of the ablated spot increases in angle). This is due to the increased reflectivity of the cornea at angles greater than 90 degrees.

The upper graph of FIG. 2 shows fluence variation with respect to the radius of corneal eye tissue, and the lower graph of FIG. 2 shows fluence variation with respect to a curved test surface such as PMMA.

Of course, instead of maintaining a consistent fluence throughout all ablation spots in a particular ablation pattern, the fluence may instead be controllably varied across the ablation pattern on a pulse-by-pulse basis, consistent with a predetermined treatment.

Fluence control and variation over a single ablation pattern on a single layer of tissue provides further and advanced ability to customize ablation treatments. For instance, irregularities on an individual's cornea can and usually are patient specific, and a goal of custom ablation surgery is to remove those unique irregularities that are detrimental to the vision of a particular patient. Topography, wavefront, or other tissue mapping techniques may be used to provide information relating to bumps, pits and other irregularities on the target surface, and fluence compensation at the relevant bumps or pits may be adjusted and actively controlled on an ablation pulse-by-ablation pulse basis to correct for such patient specific irregularities. Thus, in accordance with the principles of the present invention, custom ablation techniques can be augmented and/or implemented by actively controlling fluence across individual ablation patterns on individual tissue layers.

Apparatus and methods in accordance with the principles of the present invention are capable of correcting ametropia.

The laser source 20 may be any suitable ablation laser. For instance, an exemplary laser source 20 is a compact argon fluoride excimer laser (at 193 nm) with repetition rate of (1-1,000) Hz having an output energy range of 0.1 mJ/cm$^2$ to 1 J/cm$^2$ with a pulse width of 1–100 ns. Although the exemplary laser source 20 is an excimer laser, the laser source 20 may be any suitable laser, e.g., liquid, gas or solid-state laser source.

The laser source 20 may also include compact, optically-pumped (either flash-lamp or laser-diode pumped) lasers of Nd:YAG, Nd:YLF or the self-frequency-doubling crystal of NYAB (neodymium yttrium aluminum) with pulse duration of 0.05–20 nanoseconds and repetition rate of 1–10,000 Hz. It is known that this type of basic laser source 20 is available using a standard Q-switch or mode-lock, where the UV wavelength at 209–213 nm may be achieved by the frequency conversion techniques using nonlinear crystals. The UV laser energy required for efficient ablation ranges from 0.01 mJ to 5 mJ. The basic laser also includes an Er:YAG laser (at 2.94 microns) with repetition rate of (1–200) Hz, energy per pulse of (50–500) mJ, pulse duration of (50–400) nanoseconds and frequency-converted IR lasers of diode laser, optically-pumped Alexandrite or Li:SAF lasers, where efficient nonlinear crystals may be used to convert the fundamental wavelength (770–880 nm) into its fourth-harmonic at the UV tunable wavelength of (193–220 nm) with energy of (0.01–5.0) mJ, repetition rate of (1–10,000) and pulse duration of (0.05–150) nanoseconds. Only two non-linear crystals are needed in this case and overall efficiency is higher than that of the fifth harmonic generation which requires three nonlinear crystals.

The basic laser source 20 may also include ultrashort pulsed lasers, such as a commercialized mode-locked Ti:sapphire laser or other solid-state lasers, with wavelength ranges of (750–1100 nm), repetition rates of (0.01–100 MHz), energy per pulse of (0.01–100) microjoules, and pulse durations of (0.05–10) picoseconds where focused beam spot size of (0.05–0.5) mm is required to achieve the ablation threshold. A focused spot size of (0.05–0.5) mm of the ultrashort pulsed lasers would be appropriate to achieve the tissue ablation and precise ablation profile proposed by the present invention. The above-described lasers may also be frequency-converted into UV ranges of (190–220) nm suitable for photoablation.

The basic laser source 20 may also include a mid-IR (2.5–3.2 microns) laser generated from optical parametric oscillation (OPO) using a near-IR laser (such as Nd:YAG or Nd:YLF, flash-lamp or diode-pumped) as the pumping sources and KTP or BBO as the frequency conversion crystals. The OPO laser has advantages over the Q-switched Er:YAG laser, including higher repetition rate (10–5,000 Hz) and shorter pulse width (1–40 n.s.). These advantages provide faster surgical procedure and reduced thermal damage on the ablated corneal tissue. Typical energy per pulse of the OPO laser is (0.1–10) mJ.

To further improve the controllability of the fluence of a scanning, ablating laser beam, an optical feedback mechanism may be implemented and used in conjunction with the fluence control apparatus (e.g., aperture control and/or relay optics control) to maintain a desired spot size as the spot angles. The optical detector could also monitor the fluorescence of the cornea since the fluorescence is directly related to the fluence imparted.

The optical feedback mechanism may include an optical detector 80 to provide a feedback path between the target surface and the controller 60. The optical detector 80 provides real time images or fluorescence intensities allowing measurements of the imaged laser beam 25' on the corneal surface 10. This data is then gathered by the controller 60 for determination of spot area, and thus fluence (given a fixed laser beam power) for evaluation and control of the beam image 25' impinged onto the corneal surface 10. Of course, if the power level of the laser beam is varied on a spot-by-spot basis during the procedure, the fluence calculation may be determined appropriately.

Preferably, the optical detector 80 is a photodetector sensitized to the particular wavelength of the ablation spot (e.g., to view 193 nm laser light). Thus, the actual size of the ablation spot can be viewed by the optical detector 80, and processed by the controller 60. The spot fluence adjuster 100 may determine a desired fluence level based on the measured size of the spot or fluorescence intensity, but more particularly based on the angle of the laser beam and/or target surface. The appropriate mechanism (e.g., a controllable variable aperture 30 and/or a magnification or other characteristic of the relay optics 40) is adjusted under the direction of the controller 60 to arrive at a desired, actual fluence for that or a subsequent ablation spot.

Adjusting fluence on a pulse-by-pulse basis, or at least within a single ablation pattern on a single layer of tissue, facilitates a more precise corrective refraction procedure than is conventionally available.

The relay optics 40 may include zoom up collimators, anamorphic prisms, and the like. The relay optics 40 may be translated under the control of the controller 60. By translating the relay optics 40, the size of the image of the beam can be used to provide adjustable fluence levels on the ablation zone of the cornea 10.

For instance, as in the correction of myopia, which requires a photoablation scheme of more radiation toward the center and less around the periphery of the corneal surface, the relay optics 40 may be moved accordingly to produce an image of the laser beam having an energy density profile of more concentrated energy density toward the center of the ablation zone and having less concentrated energy around the periphery. Herein, the size of the beam is maintained while the fluence is adjusted.

Figure 3:
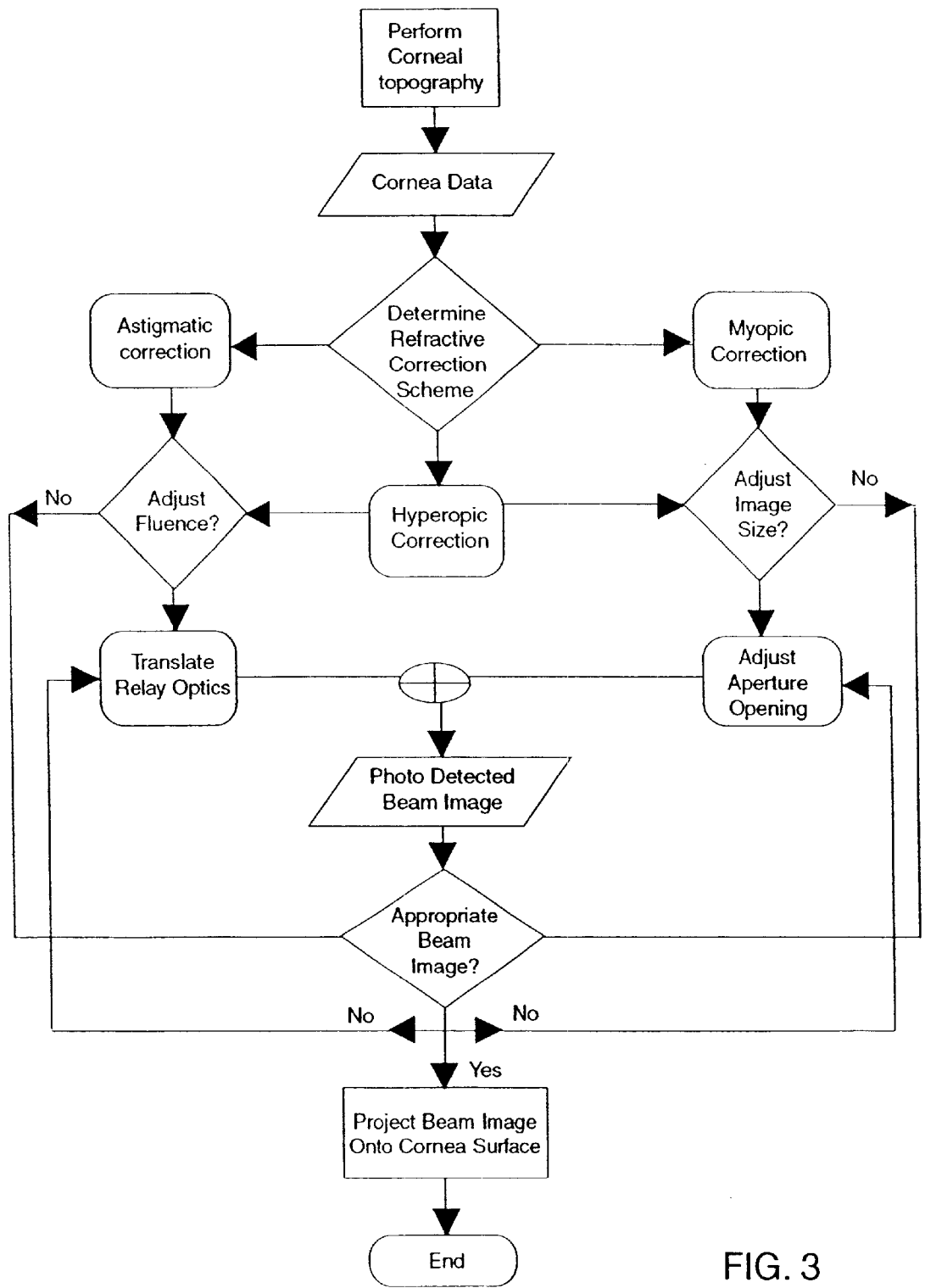
FIG. 3 is a flowchart illustrating an exemplary process of compensating for laser fluence as a laser beam scans across an ablation pattern, in accordance with the principles of the present invention.
Figure 4A:
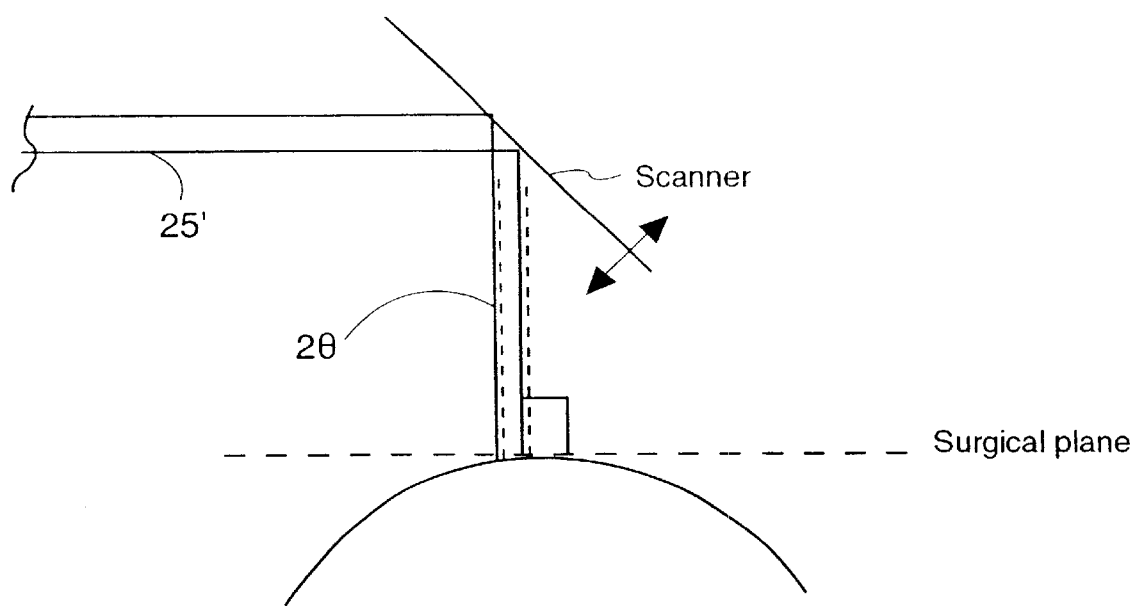
FIGS. 4A and 4B show a laser beam of a scanning laser ablation system as it places an ablation pulse in a central region of a target surface (FIG. 4A) and as it places an ablation pulse in a peripheral region of a target surface (FIG. 4B).
Figure 4B:
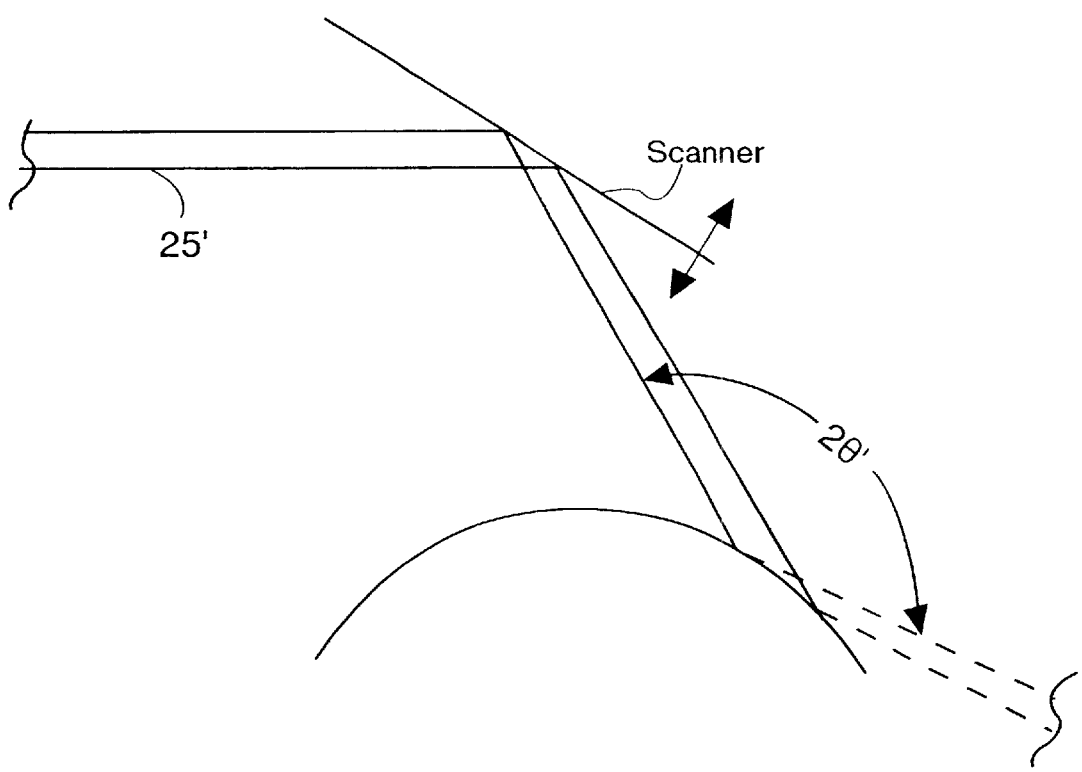

FIG. 3 illustrates an exemplary process for controlling or compensating fluence as a laser beam scans across an ablation pattern on a layer of target tissue, in accordance with the principles of the present invention.

In particular, as shown in FIG. 3, an ablating laser beam is directed along a beam path, and the energy density (i.e., fluence) is adjusted as the beam scans across a targeted ablation surface.

The present invention has particular application for custom ablation. For instance, prior to surgery, corneal topography or wavefront may be performed to collect surface feature or total eye data relating to a particular patient's eye.

The topography aides in determining the ablation pattern as well as identifying any irregularities on the corneal surface, as is otherwise know in the art.

Based on a given ablation pattern (which may or may not be determined based on customized correction of the eye), a given ablation pattern is determined. In accordance with the principles of the present invention, the ablation pattern relates not only to the number and location of ablation spots, but also to the fluence level which is to be delivered to each ablation spot.

Thus, customized topography and wavefront data may be processed by the controller 60 to determine a particular refractive corrective scheme. The refractive correction scheme will typically include the planned ablation of a plurality of layers of tissue, each layer having an ablation pattern associated therewith, and each ablation pattern having a particular fluence level associated with each ablation spot.

To further refine the delivery of exact fluence levels at each ablation spot, the controller 60 may receive real-time spot size, laser beam angle, and/or target tissue angle information from the optical detector 80.

The controller 60 then evaluates whether or not the appropriate beam image has been produced on the corneal surface. If adjustment is necessary, then the fluence of the laser beam may be adjusted in an appropriate manner, e.g., by adjusting the power level of the laser, by adjusting the attenuation level of the laser beam in a fast-acting attenuator, by adjusting a fast-acting variable aperture mechanism, by adjusting a characteristic of the relay optics, etc.

The optical detector can be placed at another location in the beam delivery path, before the laser beam impinges on the target surface, and the fluence level can be adjusted before allowed to impinge on the target surface.

While the invention has been described with reference to the exemplary embodiments thereof, those skilled in the art will be able to make various modifications to the described embodiments of the invention without departing from the true spirit and scope of the invention.

What is claimed is:

1. Apparatus to provide laser radiation on a curved surface having a desired fluence throughout, comprising:

means for providing an ablating laser beam;

means for setting a cross-sectional shape of said ablating laser beam to a first size, with respect to a particular ablation spot of a particular ablation pattern on a particular layer of tissue to provide a given fluence level for that particular ablation spot;

means for scanning said ablating laser beam to another ablation spot of said particular ablation pattern on said particular layer of tissue; and means for re-adjusting said cross-sectional shape of said ablating laser beam to a second size different from said first size, with respect to said another ablation spot, to maintain said given fluence level for said another ablation spot.

2. The apparatus to provide laser radiation on a curved surface having a desired fluence throughout according to claim 1, further comprising:

means for monitoring an image of said laser beam on said curved surface; and means for determining an area of said laser beam on said curved surface on a pulse-by-pulse basis.

3. The apparatus to provide laser radiation on a curved surface having a desired fluence throughout according to claim 1, wherein:

said means for setting and said means for re-adjusting comprise a variable aperture mechanism.

4. The apparatus to provide laser radiation on a curved surface having a desired fluence throughout according to claim 1, wherein:

said means for setting and said means for re-adjusting comprise variable magnification optics in a delivery path of said laser beam.

5. The apparatus to provide laser radiation on a curved surface having a desired fluence throughout according to claim 1, further comprising:

means for determining a fluence of an ablation spot on a pulse-by-pulse basis.

6. The apparatus to provide laser radiation on a curved surface having a desired fluence throughout according to claim 1, further comprising:

means for initially performing a topographical and/or wavefront measurement of said curved surface; and means for adjusting a fluence of said ablating laser beam based on an irregularity on said curved surface identified in said measurement.

7. A method for providing laser radiation on a curved surface having a desired fluence throughout, said method comprising:

providing an ablating laser beam;

setting a cross-sectional shape of said ablating laser beam to a first size, with respect to a particular ablation spot of a particular ablation pattern on a particular layer of tissue to provide a given fluence level for that particular ablation spot;

scanning said ablating laser beam to another ablation spot of said particular ablation pattern on said particular layer of tissue; and re-adjusting said cross-sectional shape of said ablating laser beam to a second size different from said first size, with respect to said another ablation spot, to maintain said given fluence level for said another ablation spot.

8. The method for providing laser radiation on a curved surface having a desired fluence throughout according to claim 7, further comprising:

monitoring an image of said laser beam on said curved surface; and determining an area of said laser beam on said curved surface on a pulse-by-pulse basis.

9. The method for providing laser radiation on a curved surface having a desired fluence throughout according to claim 7, wherein:

said cross-sectional shape of said ablating laser beam is adjusted with a variable aperture mechanism.

10. The method for providing laser radiation on a curved surface having a desired fluence throughout according to claim 7, wherein:

said cross-sectional shape of said ablating laser beam is adjusted by changing a magnification of relay optics in a delivery path of said laser beam.

11. The method for providing laser radiation on a curved surface having a desired fluence throughout according to claim 7, further comprising:

determining a fluence of an ablation spot on a pulse-by-pulse basis.

12. The method for providing laser radiation on a curved surface having a desired fluence throughout according to claim 7, further comprising:

initially performing a topographical and/or wavefront measurement of said curved surface; and adjusting a fluence of said ablating laser beam based on an irregularity on said curved surface identified in said measurement.

* * * * *